(12) United States Patent
Bellofatto et al.

(10) Patent No.: US 9,161,680 B2
(45) Date of Patent: Oct. 20, 2015

(54) DISPOSABLE AIR/WATER VALVE FOR AN ENDOSCOPIC DEVICE

(71) Applicant: Bracco Diagnostics Inc., Monroe Township, NJ (US)

(72) Inventors: Steven Bellofatto, Closter, NJ (US); Jeffrey B. Cushner, Woodmere, NY (US); Robert Joachim, Glen Rock, NJ (US); Scott Salmon, Tenafly, NJ (US); Kenneth E. Wolcott, Centerport, NY (US)

(73) Assignee: Bracco Diagnostics Inc., Monroe Township, NJ (US)

( * ) Notice: Subject to any disclaimer, the term of this patent is extended or adjusted under 35 U.S.C. 154(b) by 30 days.

(21) Appl. No.: 14/090,553

(22) Filed: Nov. 26, 2013

(65) Prior Publication Data

US 2015/0144215 A1    May 28, 2015

(51) Int. Cl.
  *A61B 1/00* (2006.01)
  *A61B 1/015* (2006.01)
  *F16K 11/07* (2006.01)
(52) U.S. Cl.
  CPC ............ *A61B 1/00068* (2013.01); *A61B 1/0011* (2013.01); *A61B 1/015* (2013.01); *F16K 11/0712* (2013.01); *Y10T 137/0502* (2015.04); *Y10T 137/87161* (2015.04)
(58) Field of Classification Search
  CPC .. A61B 1/015; A61B 1/0011; A61B 1/00068; F16K 11/0712; Y10T 137/87161; Y10T 137/0502
  USPC .......................................... 600/154, 159, 920
  See application file for complete search history.

(56) References Cited

U.S. PATENT DOCUMENTS

| | | |
|---|---|---|
| 3,791,379 A | 2/1974 | Storz |
| 3,924,608 A | 12/1975 | Mitsui |
| 3,958,566 A | 5/1976 | Furihata |
| 4,064,886 A | 12/1977 | Heckele |
| 4,261,343 A | 4/1981 | Ouchi et al. |
| 4,263,897 A | 4/1981 | Terayama |

(Continued)

FOREIGN PATENT DOCUMENTS

| | | |
|---|---|---|
| AU | 6526494 A | 10/1994 |
| AU | 2002244099 A1 | 7/2002 |

(Continued)

OTHER PUBLICATIONS

International Search Report and Written Opinion for Application No. PCT/US2013/071871 dated Aug. 5, 2014.

(Continued)

*Primary Examiner* — Craig Schneider
*Assistant Examiner* — Frederick D Soski
(74) *Attorney, Agent, or Firm* — Alston & Bird LLP

(57) ABSTRACT

An air/water valve assembly for use in an endoscope or other medical equipment is provided. The valve assembly includes a spool and a one-piece sealing member that includes a number of sealing rings. The spool can be injection molded, and the sealing member can be overmolded onto the spool. A spring, retainer, and housing are also included to form the valve assembly. As such, an air/water valve assembly may be made that can be used in a single medical procedure and then discarded in a cost-effective manner. Corresponding methods of manufacturing an air/water valve assembly are also provided.

20 Claims, 12 Drawing Sheets

(56) References Cited

U.S. PATENT DOCUMENTS

| | | |
|---|---|---|
| 4,270,525 A | 6/1981 | Furihata |
| 4,311,134 A | 1/1982 | Mitsui |
| 4,325,362 A | 4/1982 | Ouchi |
| 4,361,138 A | 11/1982 | Kinoshita |
| 4,408,598 A | 10/1983 | Ueda |
| 4,412,531 A | 11/1983 | Chikashige |
| 4,469,090 A | 9/1984 | Konomura |
| 4,497,550 A | 2/1985 | Ouchi et al. |
| 4,506,544 A | 3/1985 | Shimizu |
| 4,525,220 A | 6/1985 | Sasa et al. |
| 4,526,622 A | 7/1985 | Takamura et al. |
| 4,526,623 A | 7/1985 | Ishii et al. |
| 4,527,551 A | 7/1985 | Ishii |
| 4,537,182 A | 8/1985 | Otani |
| 4,545,369 A | 10/1985 | Sato |
| 4,548,197 A | 10/1985 | Kinoshita |
| 4,550,716 A | 11/1985 | Kinoshita |
| 4,552,130 A | 11/1985 | Kinoshita |
| 4,561,428 A | 12/1985 | Konomura |
| 4,562,830 A | 1/1986 | Yabe |
| 4,567,880 A | 2/1986 | Goodman |
| 4,572,163 A | 2/1986 | Collins et al. |
| 4,576,650 A | 3/1986 | Yabe et al. |
| 4,579,597 A | 4/1986 | Sasa et al. |
| 4,579,598 A | 4/1986 | Sasa et al. |
| RE32,421 E | 5/1987 | Hattori |
| 4,667,655 A | 5/1987 | Ogiu et al. |
| 4,667,691 A | 5/1987 | Sasa |
| 4,694,821 A | 9/1987 | Kondo |
| 4,736,732 A | 4/1988 | Shimonaka et al. |
| 4,741,326 A | 5/1988 | Sidall et al. |
| 4,779,624 A | 10/1988 | Yokoi |
| 4,794,913 A | 1/1989 | Shimonaka et al. |
| 4,800,869 A | 1/1989 | Nakajima |
| 4,852,551 A | 8/1989 | Opie et al. |
| 4,881,523 A | 11/1989 | Heckele |
| 4,920,953 A | 5/1990 | McGown |
| 4,971,034 A | 11/1990 | Doi et al. |
| 4,973,311 A | 11/1990 | Iwakoshi et al. |
| 4,982,726 A | 1/1991 | Taira |
| 5,020,514 A | 6/1991 | Heckele |
| 5,027,791 A | 7/1991 | Takahashi |
| 5,098,375 A | 3/1992 | Baier |
| 5,167,239 A | 12/1992 | Cohen et al. |
| 5,167,636 A | 12/1992 | Clement |
| 5,226,885 A | 7/1993 | Takahashi |
| 5,244,459 A | 9/1993 | Hill |
| 5,247,966 A | 9/1993 | Stevens et al. |
| 5,257,773 A | 11/1993 | Yoshimoto et al. |
| 5,265,840 A | 11/1993 | Gillespie |
| 5,274,874 A | 1/1994 | Cercone et al. |
| 5,282,790 A | 2/1994 | Clement |
| 5,295,956 A | 3/1994 | Bales et al. |
| 5,299,561 A | 4/1994 | Yoshimoto |
| 5,300,035 A | 4/1994 | Clement |
| 5,312,327 A | 5/1994 | Bales et al. |
| 5,312,332 A | 5/1994 | Bales et al. |
| 5,314,406 A | 5/1994 | Arias et al. |
| 5,322,263 A | 6/1994 | Yoshimoto et al. |
| 5,333,603 A | 8/1994 | Schuman |
| 5,343,854 A | 9/1994 | Katsurada |
| 5,343,855 A | 9/1994 | Iida et al. |
| 5,347,992 A | 9/1994 | Pearlman et al. |
| 5,357,946 A | 10/1994 | Kee et al. |
| 5,359,995 A | 11/1994 | Sewell, Jr. |
| 5,382,297 A | 1/1995 | Valentine et al. |
| 5,386,817 A | 2/1995 | Jones |
| 5,391,145 A | 2/1995 | Dorsey, III |
| 5,427,144 A | 6/1995 | Teets et al. |
| 5,429,596 A | 7/1995 | Arias et al. |
| 5,433,725 A | 7/1995 | Christian et al. |
| 5,447,148 A | 9/1995 | Oneda et al. |
| 5,520,636 A | 5/1996 | Korth et al. |
| 5,522,796 A | 6/1996 | Dorsey, III |
| 5,545,150 A | 8/1996 | Danks et al. |
| 5,551,448 A | 9/1996 | Matula et al. |
| 5,554,113 A | 9/1996 | Novak et al. |
| 5,601,576 A | 2/1997 | Garrison |
| 5,607,420 A | 3/1997 | Schuman |
| 5,607,440 A | 3/1997 | Danks et al. |
| 5,634,880 A | 6/1997 | Feldman et al. |
| 5,697,888 A | 12/1997 | Kobayashi et al. |
| 5,725,478 A | 3/1998 | Saad |
| 5,769,863 A | 6/1998 | Garrison |
| 5,807,238 A | 9/1998 | Feldman |
| 5,840,015 A | 11/1998 | Ogino |
| 5,860,992 A | 1/1999 | Daniel et al. |
| 5,871,441 A | 2/1999 | Ishiguro et al. |
| 5,891,014 A | 4/1999 | Akiba |
| 5,989,228 A | 11/1999 | Danks et al. |
| 6,033,413 A | 3/2000 | Mikus et al. |
| 6,047,700 A | 4/2000 | Eggers et al. |
| 6,095,971 A | 8/2000 | Takahashi |
| 6,123,689 A | 9/2000 | To et al. |
| 6,132,369 A | 10/2000 | Takahashi |
| 6,193,649 B1 | 2/2001 | Takami |
| 6,254,061 B1 | 7/2001 | Levine et al. |
| 6,286,179 B1 | 9/2001 | Byrne |
| 6,315,716 B1 | 11/2001 | Takami |
| 6,328,690 B1 | 12/2001 | Takami et al. |
| 6,334,844 B1 | 1/2002 | Akiba |
| 6,346,075 B1 | 2/2002 | Arai et al. |
| 6,354,992 B1 | 3/2002 | Kato |
| 6,358,224 B1 | 3/2002 | Tims et al. |
| 6,383,132 B1 | 5/2002 | Wimmer |
| 6,387,045 B1 | 5/2002 | Takahashi |
| 6,419,654 B1 | 7/2002 | Kadan |
| 6,428,510 B1 | 8/2002 | Kadan |
| 6,447,473 B1 | 9/2002 | Levine et al. |
| 6,533,720 B1 | 3/2003 | Dhindsa |
| 6,558,317 B2 | 5/2003 | Takahashi et al. |
| 6,666,818 B2 | 12/2003 | Dhindsa |
| 6,786,865 B2 | 9/2004 | Dhindsa |
| 6,802,809 B2 | 10/2004 | Okada |
| 6,849,043 B2 | 2/2005 | Kondo |
| 6,908,429 B2 | 6/2005 | Heimberger |
| 6,929,602 B2 | 8/2005 | Hirakui et al. |
| 7,001,331 B2 | 2/2006 | Kaji |
| 7,226,411 B2 | 6/2007 | Akiba |
| 7,318,814 B2 | 1/2008 | Levine et al. |
| 7,347,828 B2 | 3/2008 | Francese et al. |
| 7,473,219 B1 | 1/2009 | Glenn |
| 7,479,106 B2 | 1/2009 | Banik et al. |
| 7,597,688 B1 | 10/2009 | Masson |
| 7,708,938 B2 | 5/2010 | Mariotti et al. |
| 8,182,419 B2 | 5/2012 | Kohno |
| 8,231,523 B2 | 7/2012 | Uesugi et al. |
| 8,235,889 B2 | 8/2012 | Kohno |
| 8,241,208 B2 | 8/2012 | Jiang et al. |
| 8,251,945 B2 | 8/2012 | Secrest et al. |
| 8,262,565 B2 | 9/2012 | Okada |
| 8,273,014 B2 | 9/2012 | Ushijima et al. |
| 8,382,661 B2 | 2/2013 | Yamane |
| 8,414,478 B2 | 4/2013 | Yamane |
| 8,454,498 B2 | 6/2013 | Cushner et al. |
| 2002/0035391 A1 | 3/2002 | Mikus et al. |
| 2002/0095069 A1 | 7/2002 | Dhindsa |
| 2002/0107457 A1 | 8/2002 | Francese et al. |
| 2002/0188175 A1 | 12/2002 | Levine et al. |
| 2003/0181786 A1 | 9/2003 | Heimberger |
| 2003/0181787 A1 | 9/2003 | Kondo |
| 2003/0216617 A1 | 11/2003 | Hirakui et al. |
| 2004/0238014 A1 | 12/2004 | Halstead et al. |
| 2005/0079094 A1 | 4/2005 | Mariotti |
| 2005/0096504 A1 | 5/2005 | Akiba |
| 2005/0143817 A1 | 6/2005 | Hunter et al. |
| 2005/0149080 A1 | 7/2005 | Hunter et al. |
| 2005/0149158 A1 | 7/2005 | Hunter et al. |
| 2005/0165488 A1 | 7/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |

(56) References Cited

U.S. PATENT DOCUMENTS

| | | |
|---|---|---|
| 2005/0183728 A1 | 8/2005 | Hunter et al. |
| 2005/0191331 A1 | 9/2005 | Hunter et al. |
| 2005/0245789 A1 | 11/2005 | Smith et al. |
| 2005/0267417 A1 | 12/2005 | Secrest et al. |
| 2006/0009680 A1 | 1/2006 | Dhindsa |
| 2006/0041190 A1 | 2/2006 | Sato |
| 2006/0100485 A1 | 5/2006 | Arai et al. |
| 2006/0116552 A1 | 6/2006 | Noguchi et al. |
| 2006/0135851 A1 | 6/2006 | Yamazaki |
| 2006/0147492 A1 | 7/2006 | Hunter et al. |
| 2006/0217637 A1 | 9/2006 | Leiboff et al. |
| 2006/0247500 A1 | 11/2006 | Voegele et al. |
| 2007/0006883 A1 | 1/2007 | Kolb et al. |
| 2007/0156121 A1 | 7/2007 | Millman et al. |
| 2007/0173861 A1 | 7/2007 | Strommer et al. |
| 2007/0179432 A1 | 8/2007 | Bar et al. |
| 2007/0219630 A1 | 9/2007 | Chu |
| 2007/0232859 A1 | 10/2007 | Secrest et al. |
| 2007/0244359 A1 | 10/2007 | Cabiri et al. |
| 2007/0249993 A1 | 10/2007 | Mollstam et al. |
| 2007/0282168 A1 | 12/2007 | Kaye et al. |
| 2008/0021280 A1 | 1/2008 | Suzuki |
| 2008/0243054 A1 | 10/2008 | Mollstam et al. |
| 2009/0099520 A1 | 4/2009 | Millman et al. |
| 2009/0137943 A1 | 5/2009 | Stearns et al. |
| 2009/0216084 A1 | 8/2009 | Yamane |
| 2010/0056867 A1 | 3/2010 | Labombard et al. |
| 2010/0094200 A1 | 4/2010 | Dean et al. |
| 2010/0129316 A1 | 5/2010 | Levitt |
| 2010/0185139 A1 | 7/2010 | Stearns |
| 2010/0198346 A1 | 8/2010 | Keogh et al. |
| 2011/0071357 A1 | 3/2011 | Ushijima |
| 2011/0208003 A1 | 8/2011 | Yamane |
| 2012/0018011 A1 | 1/2012 | Koga |
| 2012/0071843 A1 | 3/2012 | Yamane |
| 2012/0071844 A1 | 3/2012 | Yamane |
| 2012/0085956 A1 | 4/2012 | Morimoto |
| 2012/0088973 A1 | 4/2012 | Morimoto |
| 2012/0088975 A1 | 4/2012 | Morimoto |
| 2012/0101336 A1 | 4/2012 | Hirsch et al. |
| 2013/0138061 A1 | 5/2013 | Yamane |
| 2013/0303844 A1 | 11/2013 | Grudo et al. |
| 2013/0338442 A1 | 12/2013 | Anderson et al. |

FOREIGN PATENT DOCUMENTS

| | | |
|---|---|---|
| AU | 2003284135 A8 | 5/2004 |
| AU | 2004315565 B2 | 5/2008 |
| AU | 2011336623 A1 | 6/2013 |
| AU | 2011336701 A1 | 7/2013 |
| CA | 2 159 598 A1 | 10/1994 |
| CA | 2 434 519 A1 | 7/2002 |
| CA | 2 818 985 A1 | 6/2012 |
| CA | 2 819 192 A1 | 6/2012 |
| CN | 1176141 A | 3/1998 |
| CN | 2538293 Y | 3/2003 |
| CN | 2745525 Y | 12/2005 |
| CN | 101194824 A | 6/2008 |
| CN | 101322635 A | 12/2008 |
| CN | 201519130 U | 7/2010 |
| CN | 102131451 A | 7/2011 |
| CN | 102397048 A | 4/2012 |
| CN | 102406497 A | 4/2012 |
| CN | 102406498 A | 4/2012 |
| CN | 202288226 U | 7/2012 |
| CN | 202335846 U | 7/2012 |
| CN | 202376065 U | 8/2012 |
| DE | 3923243 A1 | 1/1991 |
| DE | 20214968 U1 | 2/2004 |
| DE | 202006013987 U1 | 1/2007 |
| EP | 0 055 394 A1 | 7/1982 |
| EP | 0 072 257 A2 | 2/1983 |
| EP | 0 024 706 B1 | 6/1984 |
| EP | 0 055 393 B1 | 7/1984 |
| EP | 0 075 275 A3 | 8/1984 |
| EP | 0 056 234 B1 | 1/1985 |
| EP | 0 025 958 B1 | 3/1985 |
| EP | 0 075 188 B1 | 11/1987 |
| EP | 0 189 947 B1 | 8/1989 |
| EP | 0 998 212 B1 | 4/2002 |
| EP | 1 346 681 A3 | 6/2005 |
| EP | 1 741 460 A1 | 1/2007 |
| EP | 1 813 184 A1 | 8/2007 |
| EP | 1 882 442 A1 | 1/2008 |
| EP | 1 882 443 A1 | 1/2008 |
| EP | 1 991 288 A2 | 11/2008 |
| EP | 1 355 687 B1 | 3/2009 |
| EP | 1 652 464 B1 | 7/2009 |
| EP | 2 095 757 A1 | 9/2009 |
| EP | 1 077 041 B1 | 11/2010 |
| EP | 2 335 552 A1 | 6/2011 |
| EP | 2 433 550 A1 | 3/2012 |
| EP | 2 441 376 A1 | 4/2012 |
| EP | 2 441 377 A1 | 4/2012 |
| EP | 2 441 379 A1 | 4/2012 |
| FR | 2 884 150 A1 | 10/2006 |
| GB | 1 427 962 A | 3/1976 |
| GB | 2 418 521 A | 3/2006 |
| IN | 161794 A1 | 2/1988 |
| JP | 58-10031 A | 1/1983 |
| JP | 58-50933 A | 3/1983 |
| JP | 58-133229 A | 8/1983 |
| JP | 60-142835 A | 7/1985 |
| JP | 63-249543 A | 10/1988 |
| JP | 3-114430 A | 5/1991 |
| JP | 4-2323 A | 1/1992 |
| JP | 4-371162 A | 12/1992 |
| JP | 5-199984 A | 8/1993 |
| JP | 5-199985 A | 8/1993 |
| JP | 5-199986 A | 8/1993 |
| JP | 5-228103 A | 9/1993 |
| JP | 6-14871 A | 1/1994 |
| JP | 6-70880 A | 3/1994 |
| JP | 6-189899 A | 7/1994 |
| JP | 6-304130 A | 11/1994 |
| JP | 7-349 A | 1/1995 |
| JP | 7-23897 A | 1/1995 |
| JP | 7-23898 A | 1/1995 |
| JP | 7-51222 A | 2/1995 |
| JP | 7-327919 A | 12/1995 |
| JP | 8-550 A | 1/1996 |
| JP | 8-56899 A | 3/1996 |
| JP | 8-71037 A | 3/1996 |
| JP | 8-112250 A | 5/1996 |
| JP | 8-117182 A | 5/1996 |
| JP | 8-238213 A | 9/1996 |
| JP | 9-38022 A | 2/1997 |
| JP | 9-84741 A | 3/1997 |
| JP | 9-84756 A | 3/1997 |
| JP | 9-164111 A | 6/1997 |
| JP | 9-220194 A | 8/1997 |
| JP | 10-33468 A | 2/1998 |
| JP | 10-52398 A | 2/1998 |
| JP | 10-52399 A | 2/1998 |
| JP | 10-225431 A | 8/1998 |
| JP | 10-328132 A | 12/1998 |
| JP | 11-56767 A | 3/1999 |
| JP | 11-56769 A | 3/1999 |
| JP | 11-123174 A | 5/1999 |
| JP | 11-164810 A | 6/1999 |
| JP | 11-216104 A | 8/1999 |
| JP | 2000-70218 A | 3/2000 |
| JP | 2000-271079 A | 10/2000 |
| JP | 2000-287917 A | 10/2000 |
| JP | 2000-287918 A | 10/2000 |
| JP | 2001-54502 A | 2/2001 |
| JP | 2001-61771 A | 3/2001 |
| JP | 2001-61772 A | 3/2001 |
| JP | 2001-61773 A | 3/2001 |
| JP | 2001-78957 A | 3/2001 |
| JP | 2001-157663 A | 6/2001 |
| JP | 2001-275943 A | 10/2001 |
| JP | 2001-321333 A | 11/2001 |

(56) References Cited

FOREIGN PATENT DOCUMENTS

| | | |
|---|---|---|
| JP | 2002-17662 A | 1/2002 |
| JP | 2002-143086 A | 5/2002 |
| JP | 2002-172086 A | 6/2002 |
| JP | 2003-250746 A | 9/2003 |
| JP | 2003-275172 A | 9/2003 |
| JP | 2003-305003 A | 10/2003 |
| JP | 2003-310541 A | 11/2003 |
| JP | 2004-049757 A | 2/2004 |
| JP | 2004-073259 A | 3/2004 |
| JP | 2004-141303 A | 5/2004 |
| JP | 2004-141304 A | 5/2004 |
| JP | 2004-141331 A | 5/2004 |
| JP | 2004-223121 A | 8/2004 |
| JP | 2005-58547 A | 3/2005 |
| JP | 2005-218668 A | 8/2005 |
| JP | 2005-261512 A | 9/2005 |
| JP | 2005-270216 A | 10/2005 |
| JP | 2005-319056 A | 11/2005 |
| JP | 2006-524 A | 1/2006 |
| JP | 2006-525 A | 1/2006 |
| JP | 2006-526 A | 1/2006 |
| JP | 2006-141935 A | 6/2006 |
| JP | 2006-175175 A | 7/2006 |
| JP | 2007-14439 A | 1/2007 |
| JP | 2007-75417 A | 3/2007 |
| JP | 2007-190054 A | 8/2007 |
| JP | 2007-190055 A | 8/2007 |
| JP | 2007-229010 A | 9/2007 |
| JP | 2008-48796 A | 3/2008 |
| JP | 2008-142212 A | 6/2008 |
| JP | 2008-307250 A | 12/2008 |
| JP | 2009-45102 A | 3/2009 |
| JP | 2009-45126 A | 3/2009 |
| JP | 2009-45130 A | 3/2009 |
| JP | 2009-89765 A | 4/2009 |
| JP | 2009-232896 A | 10/2009 |
| JP | 2009-254631 A | 11/2009 |
| JP | 2010-284299 A | 12/2010 |
| JP | 2011-167350 A | 9/2011 |
| JP | 2012-24245 A | 2/2012 |
| KR | 2002-0038662 A | 5/2002 |
| MX | PA03006417 A | 12/2004 |
| NL | 2005411 C | 3/2012 |
| RU | 115 202 U1 | 10/1994 |
| RU | 2 424 761 C1 | 7/2011 |
| WO | WO-94/22358 A1 | 10/1994 |
| WO | WO-02/56942 B1 | 4/2004 |
| WO | WO-2004/034873 A3 | 2/2005 |
| WO | WO-2006/063245 A9 | 8/2006 |
| WO | WO-2007/103057 A3 | 3/2008 |
| WO | WO 2010/111546 A2 | 9/2010 |
| WO | WO-2010/116563 A1 | 10/2010 |
| WO | WO-2012/075116 A1 | 6/2012 |
| WO | WO-2012/075131 A1 | 6/2012 |
| WO | WO-2013/099445 A1 | 7/2013 |

OTHER PUBLICATIONS

Evis Exera GIF/CF/PCF Type 160 Series Operation Manual, Olympus (2003) 95 pages.
Endoscope Channel Guide, Exera Evis 40/140/240 & Exera 160-Series GI Endoscopes, Olympus (2003) 1 page.
"*Endoscope Channel Guide—Evis 40/140/240 & Exera 160-Series GI Endoscopes*;" Olympus America, Inc.; dated 2003.
International Search Report for Application No. PCT/US2011/062628; dated Mar. 27, 2012.
U.S. Appl. No. 13/989,573, filed May 24, 2013; first named inventor: Anderson.

DISPOSABLE AIR/WATER VALVE FOR AN ENDOSCOPIC DEVICE

FIELD OF THE INVENTION

The present invention relates generally to air/water valves for use with medical instruments. More particularly the present invention relates to a disposable valve assembly for use in an endoscopic device.

BACKGROUND OF THE INVENTION

Endoscopes are used in modern medical practices to allow a medical practitioner to look inside a hollow organ or body cavity of a patient. Using an endoscope, a patient's symptoms may be investigated (e.g., symptoms in the digestive system including nausea, vomiting, abdominal pain, difficulty swallowing, gastrointestinal bleeding, etc.); a diagnosis may be confirmed (e.g., by performing a biopsy); or treatment may be provided (e.g., cauterizing a bleeding vessel, widening a narrow esophagus, clipping off a polyp, etc.).

Unlike other medical imaging devices, endoscopes are inserted directly into the organ or cavity. During an endoscopic procedure, air and water are typically used to insufflate the organ or cavity being accessed and/or to irrigate the area and/or portions of the device (e.g., the optic head of the endoscope itself). The flow of air and water is typically controlled by the user of the device via a valve.

SUMMARY OF THE INVENTION

Valves such as those described above for regulating the flow of air and water through an endoscope must be cleaned and disinfected after every medical procedure to avoid cross-contamination between patients. This necessitates having several valves on hand to accommodate back-to-back procedures, as the cleaning and disinfection processes can take significant time to complete. Reusable valves are also expensive and must be handled with care.

Accordingly, embodiments of the present invention described herein provide for a disposable valve assembly for regulating the flow of air and water through a medical instrument, such as an endoscope. Embodiments of the valve assembly described herein are designed for use in a single procedure and can then be discarded.

As described below, in one embodiment, a valve assembly for a medical instrument is provided that includes a housing and a spool comprising a first end, a second end, a longitudinal passageway extending between the first end and the second end, and first and second portions proximate the first and second ends, respectively. The first portion of the spool may be configured to be received at least partially within the housing, and an outer surface of the second portion of the spool may define a plurality of positioning features. The valve assembly may further include a sealing member comprising a longitudinal support member and a plurality of sealing rings extending circumferentially from the support member. Each sealing ring may be spaced from an adjacent sealing ring a distance along a length of the support member that corresponds to a distance between adjacent positioning features. An inner surface of the support member may be configured to engage the outer surface of the spool. Furthermore, each sealing ring may define an opening such that an inner circumferential surface of each sealing ring is configured to sealingly engage the outer surface of the second portion of the spool proximate a corresponding positioning feature.

In some cases, the valve assembly may further include a spring and a retainer. The spring may comprise a first end and a second end and may be disposed around the first portion of the spool. The retainer may be configured to be received by the first end of the spool. The second end of the spring may be configured to engage and remain fixed with respect to the housing, and the first end of the spring may be configured to engage the retainer, such that the retainer is biased away from the housing. The housing may define at least one radial extension configured to engage the second end of the spring. At least a portion of the outer surface of the spool may define a longitudinal groove configured to receive the support member of the sealing member. An outer surface of the support member may form a flush surface with the outer surface of the spool when the sealing member is engaged with the spool. Furthermore, the sealing member may be overmolded onto the spool.

In some embodiments, the spool may define a transverse passageway that is substantially perpendicular and intersects with the longitudinal passageway. The transverse passageway may be defined through the longitudinal groove. At least one portion of the longitudinal groove may be defined by at least one positioning feature. In addition, the spool may define a transverse passageway that is substantially perpendicular to and intersects with the longitudinal passageway, and the support member of the sealing member may define a longitudinally extending ring configured to engage an opening of the transverse passageway defined in the outer surface of the spool.

The sealing member may comprise four sealing rings in some cases. In addition, the housing may define longitudinal extensions that are configured to engage an endoscope within which the valve assembly is mounted.

In other embodiments, a method of manufacturing a valve assembly for a medical instrument is provided. The method may include molding a spool, where the spool comprises a first end, a second end, a longitudinal passageway extending between the first end and the second end, and first and second portions proximate the first and second ends, respectively. An outer surface of the second portion of the spool may define a plurality of positioning features.

The method may further include overmolding a sealing member onto an outer surface of the spool. The sealing member may comprise a longitudinal support member and a plurality of sealing rings extending circumferentially from the support member. Each sealing ring may be spaced from an adjacent sealing ring a distance along a length of the support member that corresponds to a distance between adjacent positioning features. An inner surface of the support member may engage the outer surface of the spool, and each sealing ring may define an opening such that an inner circumferential surface of each sealing ring may sealingly engage the outer surface of the second portion of the spool proximate a corresponding positioning feature. Furthermore, a housing may be molded that is configured to at least partially receive the first portion of the spool, and the first portion of the spool may be disposed at least partially within the housing.

In some cases, the method may include disposing a spring around the first portion of the spool, wherein the spring defines a first end and a second end, and providing a retainer configured to be received by the first end of the spool. The second end of the spring may be engaged to the housing such that a position of the second end of the spring remains fixed with respect to the housing, and the first end of the spring may be engaged with the retainer. The retainer may be attached to the first end of the spool, such that the retainer is biased away from the housing.

In some embodiments, a longitudinal groove may be defined in at least a portion of the outer surface of the spool, wherein the longitudinal groove is configured to receive the support member of the sealing member. Molding the spool may comprise using a first mold to form the spool, and overmolding the sealing member may comprise removing the spool from the first mold and placing the spool in a second mold. Overmolding the sealing member may comprise directing an elastomeric material into the longitudinal groove to form the sealing member in the second mold.

In some cases, a plurality of stationary plates may be arranged in an orientation that is perpendicular to a longitudinal axis of the spool. The plates may comprise concentric holes and may be positioned at locations corresponding to locations of the sealing rings to be formed. Moreover, molding the spool may comprise defining a transverse passageway that is substantially perpendicular to and intersects with the longitudinal passageway, and wherein the transverse passageway is defined through the longitudinal groove. At least one portion of the longitudinal groove may be defined by at least one positioning feature. Additionally or alternatively, molding the spool may comprise defining a transverse passageway that is substantially perpendicular and intersects with the longitudinal passageway, and overmolding the sealing member may comprise defining a longitudinally extending ring in the support member that engages an opening of the transverse passageway defined in the outer surface of the spool.

Such embodiments provide significant advantages as described and otherwise discussed herein.

BRIEF DESCRIPTION OF THE DRAWINGS

Reference will now be made to the accompanying drawings, which are not necessarily drawn to scale. The drawings are for illustrative purposes only, and are not intended to limit the scope of the present invention.

DETAILED DESCRIPTION OF THE INVENTION

Embodiments of the present invention will be described with reference to the accompanying drawings, where applicable. It is understood that the present invention may be embodied in many different forms and should not be construed as limited to the embodiments set forth herein; rather, these embodiments are provided for illustrative purposes only. Like numbers refer to like elements throughout.

While the embodiments of the valve assembly and method for making the valve assembly for regulating the flow of air and water through a medical instrument are described below in the context of an endoscope for performing an endoscopic procedure (such as a colonoscopy), it should be understood that the embodiments of the present invention may also be utilized in other medical instruments including, for example, a variety of different endoscopic and/or laparoscopic instruments.

Figure 1:
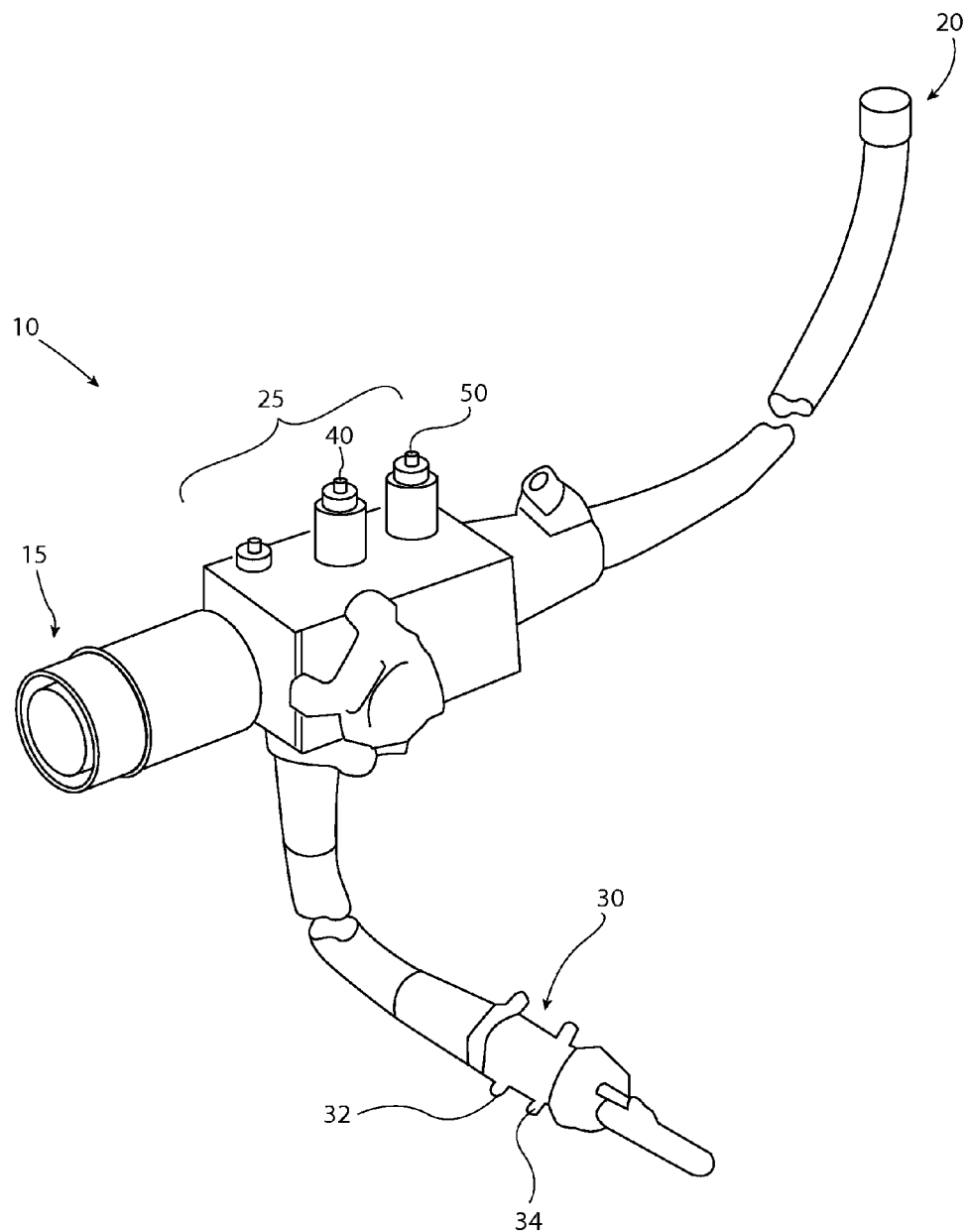
FIG. 1 shows a schematic illustration of an endoscopic device.

An example of an endoscope 10 for performing endoscopic procedures, such as a gastrointestinal endoscopy, is shown in FIG. 1. The depicted endoscope 10 includes a proximal end 15, which may be the end closest to the user (e.g., the medical practitioner) and may include an eyepiece that the user can look through to view the organ or cavity being examined. The endoscope 10 also includes a distal end 20, which may be the end closest to the target site within the organ or cavity being examined. Controls may be provided on a main body 25 of the endoscope disposed between the proximal and distal ends 15, 20. Furthermore, a fluid conducting portion 30 may be provided that connects a source of air and water (not shown) with the distal end 20 of the endoscope 10. For example, air, $CO_2$, or other gas for distending the organ or cavity is able to enter the endoscope 10 via a gas inlet 32, and water is able to enter via a water inlet 34. The flow of either fluid towards the distal end 20 may be regulated and controlled via the user's interaction with the controls of the main body 25. The main body 25 of the endoscope 10 may house a suction valve 40 for withdrawing effluent and gases from the gastrointestinal tract, as well as an air/water valve 50 for controlling the flow of air and/or water through the endoscope.

Figures 2A, 2B:
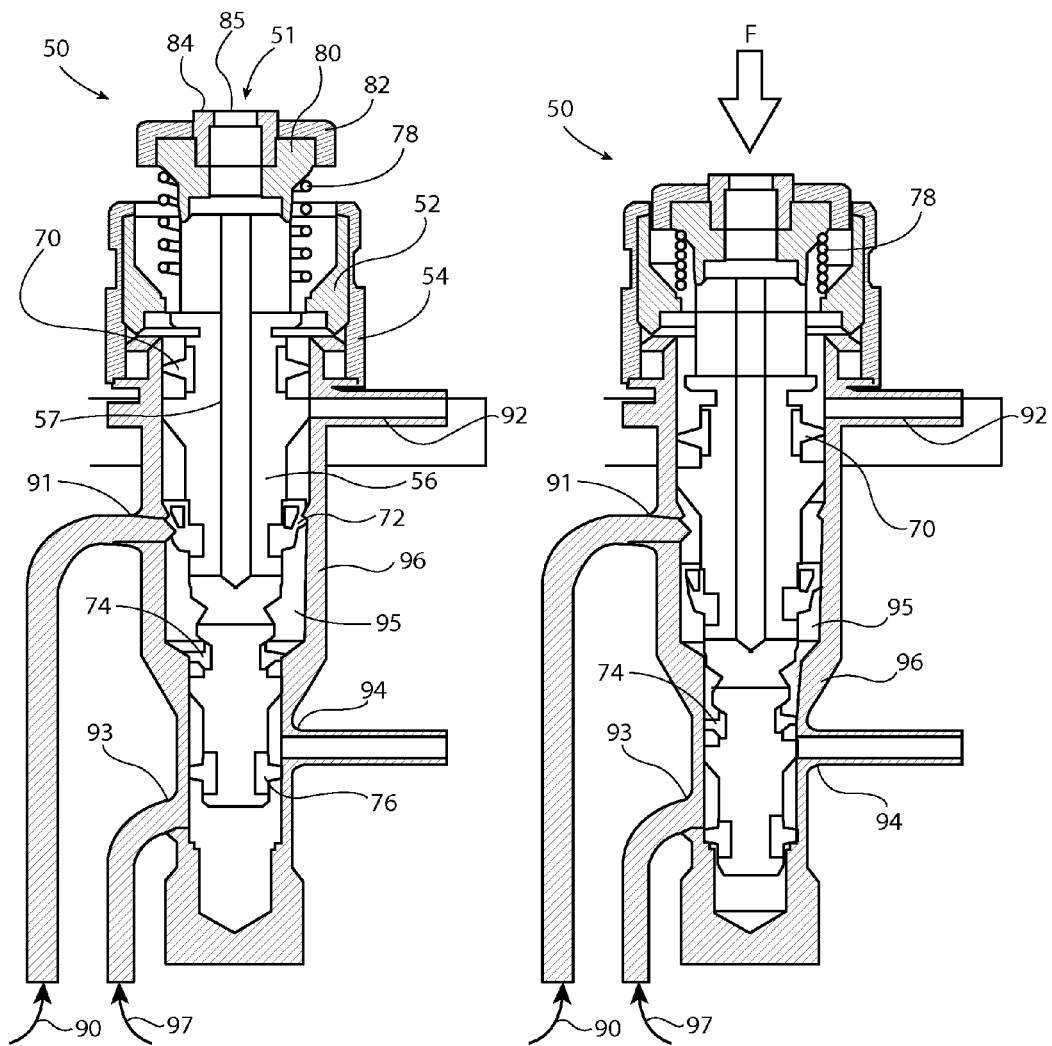
FIG. 2A shows a cross-sectional view of a conventional air/water valve assembly in an unactuated position.
FIG. 2B shows a cross-sectional view of the air/water valve assembly of FIG. 2A in an actuated position.

The operation of the air/water valve 50 is shown in the cross-sectional views of FIGS. 2A and 2B. For example, an unactuated position of the valve 50 is shown in FIG. 2A, and an actuated position of the valve is shown in FIG. 2B. As illustrated in FIG. 2A, a spring 78 may be provided that engages a spring retainer 80 at one end and a valve housing 52, 54 at the other end. The spring retainer 80 may be attached to the spool 56 (e.g., via other valve components shown in FIG. 3), such that the spring 78 biases the spool 56 to the unactuated position shown in FIG. 2A. At the same time, an actuation force F applied to the outer end 51 of the valve 50 by the user (as shown in FIG. 2B) may serve to move the spool 56 and its components with respect to the housing 52, 54 to the actuated position of FIG. 2B.

As shown in FIGS. 2A and 2B, at least a portion of the spool 56 is configured to define a passageway 57 therethrough. The spool 56 may, for example, define a port 59 that is oriented perpendicularly with respect to the longitudinal axis of the passageway 57 of the spool 56, and the passageway 57 may extend from the port 59 to an opening 85 at the outer end 51 of the valve 50.

With reference to FIG. 2A, air 90 (or other gas) may be able to flow from the gas inlet 32 (shown in FIG. 1) into a cavity 95 defined by an air/water cylinder 96 in which the valve 50 is disposed via an inlet 91. When the opening 85 is clear (e.g., when the user is not blocking the opening 85 with a finger, for example), the air 90 may flow from the cavity 95, through the port 59, through the passageway 57, and out of the valve assembly via the opening 85. When the opening 85 is blocked by the user's finger, for example, pressure within the passageway 57 may build up to a point at which the air 90 is forced past a lip seal 72 that is positioned around the spool 56 (e.g., by deflecting the seal away from the inner surface of the air/water cylinder 96, towards the spool 56) and out of the cavity 95 past the bearing 70 towards an outlet in the distal end 20 of the endoscope via an outlet 92. At the same time, the flow of water 97 from an inlet 93 is precluded from exiting the cavity 95 via an outlet 94, as the seal 76 (shown also in FIG. 4) does not allow the air to flow past.

When the user applies a force F against the biasing force of the spring 78 to actuate the valve 50, the valve is moved to the actuated position shown in FIG. 2B. In the actuated position, air 90 is precluded from exiting the cavity 95 via outlet 92 as a result of the movement of a seal 70 to a position shown in FIG. 2B that blocks the air from accessing the outlet 92. In addition, the seal 76 that was blocking the passage of water from the inlet 93 to the outlet 94 of the air/water cylinder 96 is also moved so as to clear a pathway for the flow of water to the outlet 94. In the actuated position shown in FIG. 2B, the seal 74 blocks the water from the inlet 92 from passing into the space in the cavity 95 through which the airflow path from the inlet 91 to the outlet 92 is defined.

Figure 3:
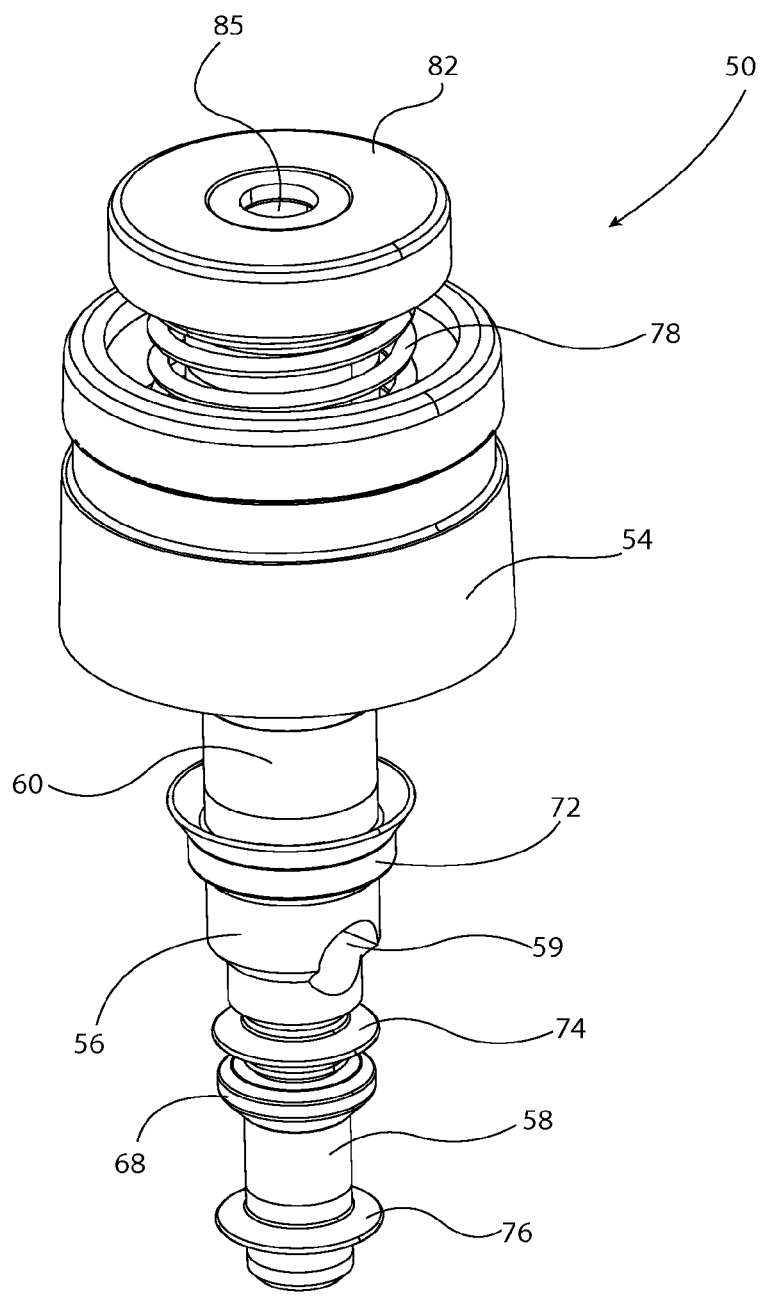
FIG. 3 shows a perspective view of a conventional air/water valve assembly.
Figure 4:
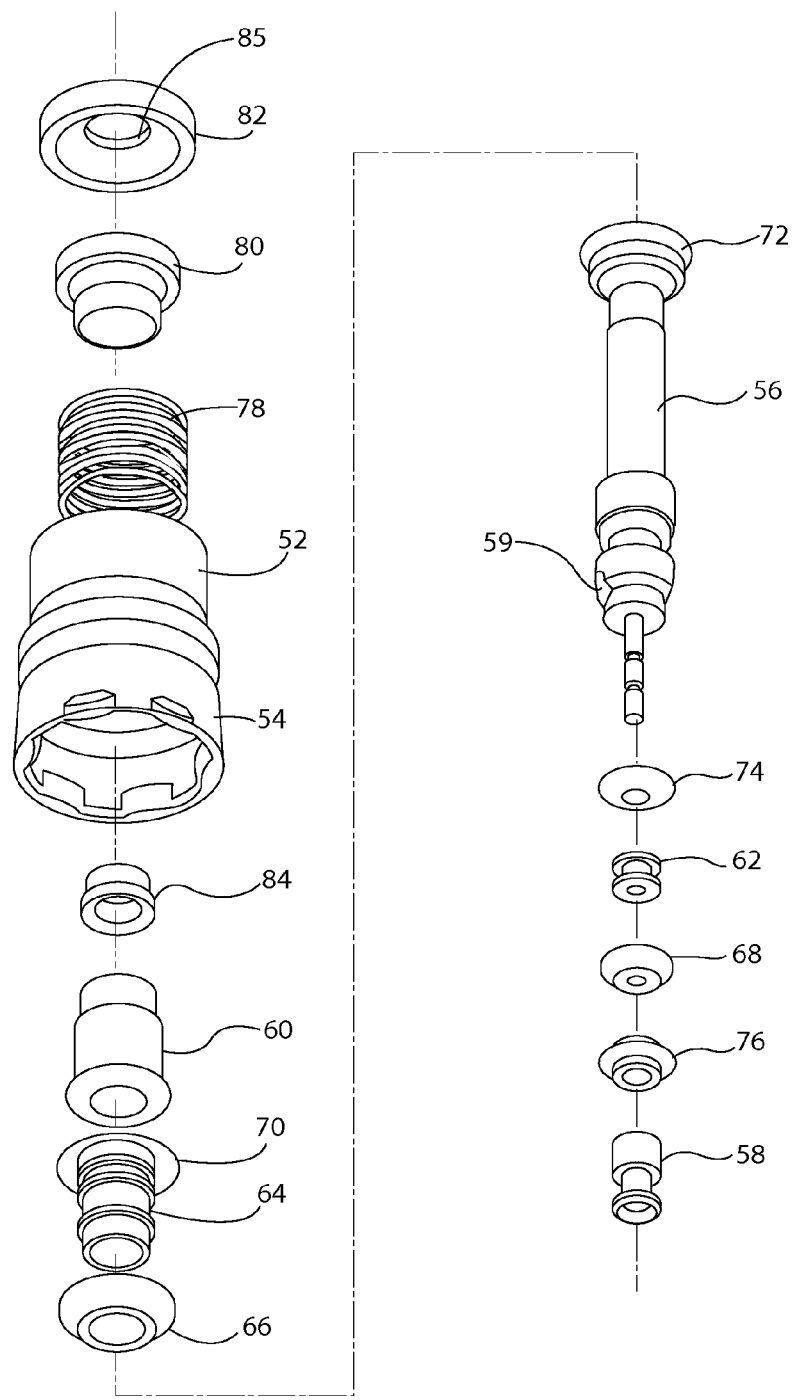
FIG. 4 shows an exploded view of the air/water valve assembly of FIG. 3.

With reference now to FIGS. 3 and 4, a conventional reusable air/water valve 50, as described above, is shown in assembled and exploded configurations. Conventional reusable valves 50 typically include a number of machined metal parts that, along with multiple seals, must be assembled together to form a valve that is able to function as described above with respect to FIGS. 2A and 2B. For example, the depicted valve (shown in exploded form in FIG. 4) includes a housing 52 and a housing overmold 54; a spool 56 with spool ends 58, 60 and spool sleeves; two bearings 66, 68; four seals 70, 72, 74, 76; a spring 78, spring retainer 80, and retainer cap 82; and a color ring 84 for a total of seventeen separate components. Of these components, six are machined metal components (e.g., the housing 52, the spool 56, the spool ends 58, 60, and the spool sleeves 62, 64). The large number of components results in a complex design that is costly to fabricate and laborious to assemble. Moreover, the reusable nature of the valve 50 requires the valve to be cleaned and disinfected after every use to prevent cross-contamination between patients, which also adds to the cost.

Accordingly embodiments of the present invention provide an air/water valve that is made up of fewer components than conventional reusable valves such as the example described above and shown in FIGS. 2A-4. Moreover, in embodiments of the present invention, all of the components can be produced using injection molding, thereby eliminating the need for machined metal parts. In this way, embodiments of the present invention provide a valve that can be used as a disposable (e.g., single-use) valve in a cost-effective manner.

Figure 5:
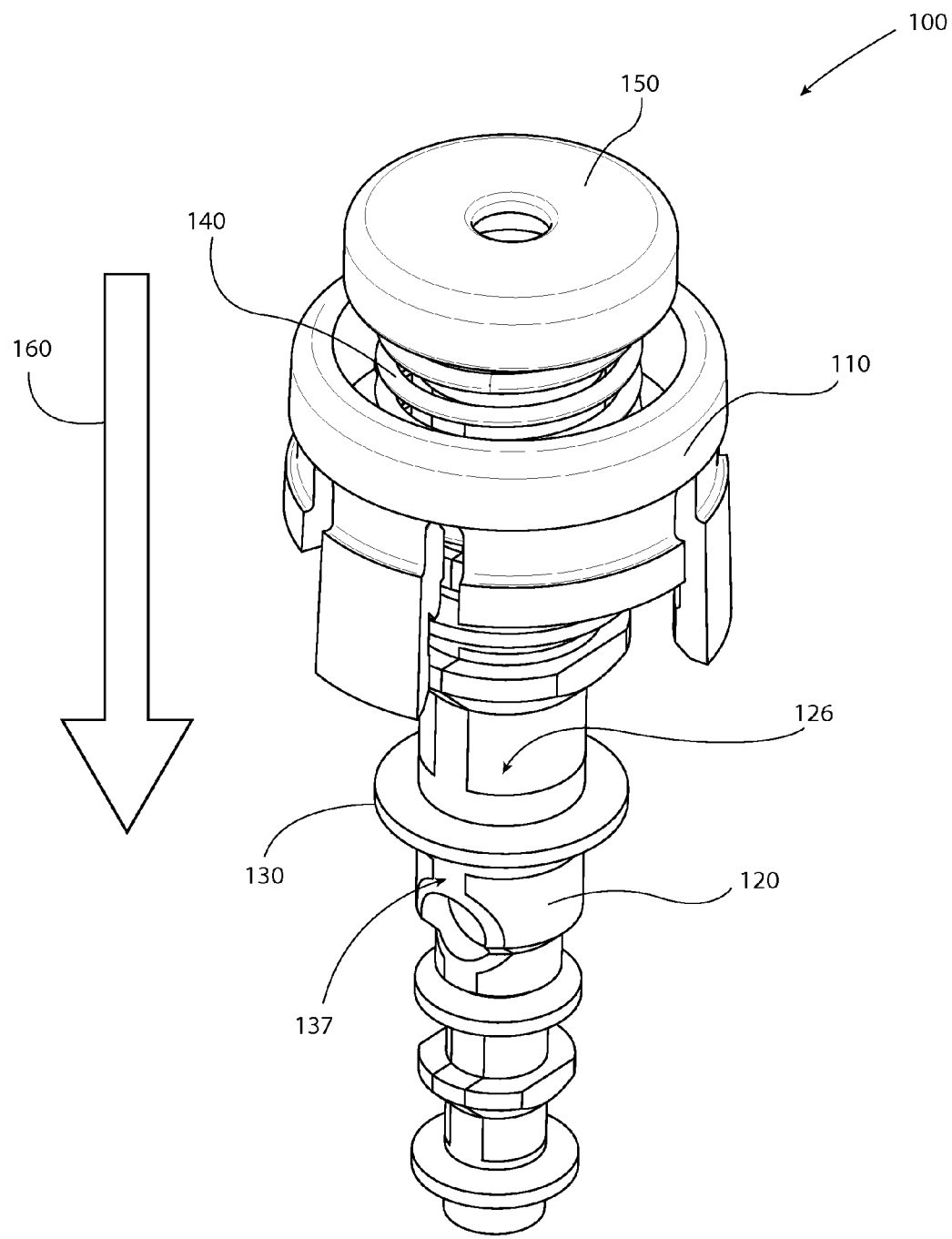
FIG. 5 shows a perspective view of an air/water valve assembly according to an exemplary embodiment of the present invention.
Figure 6:
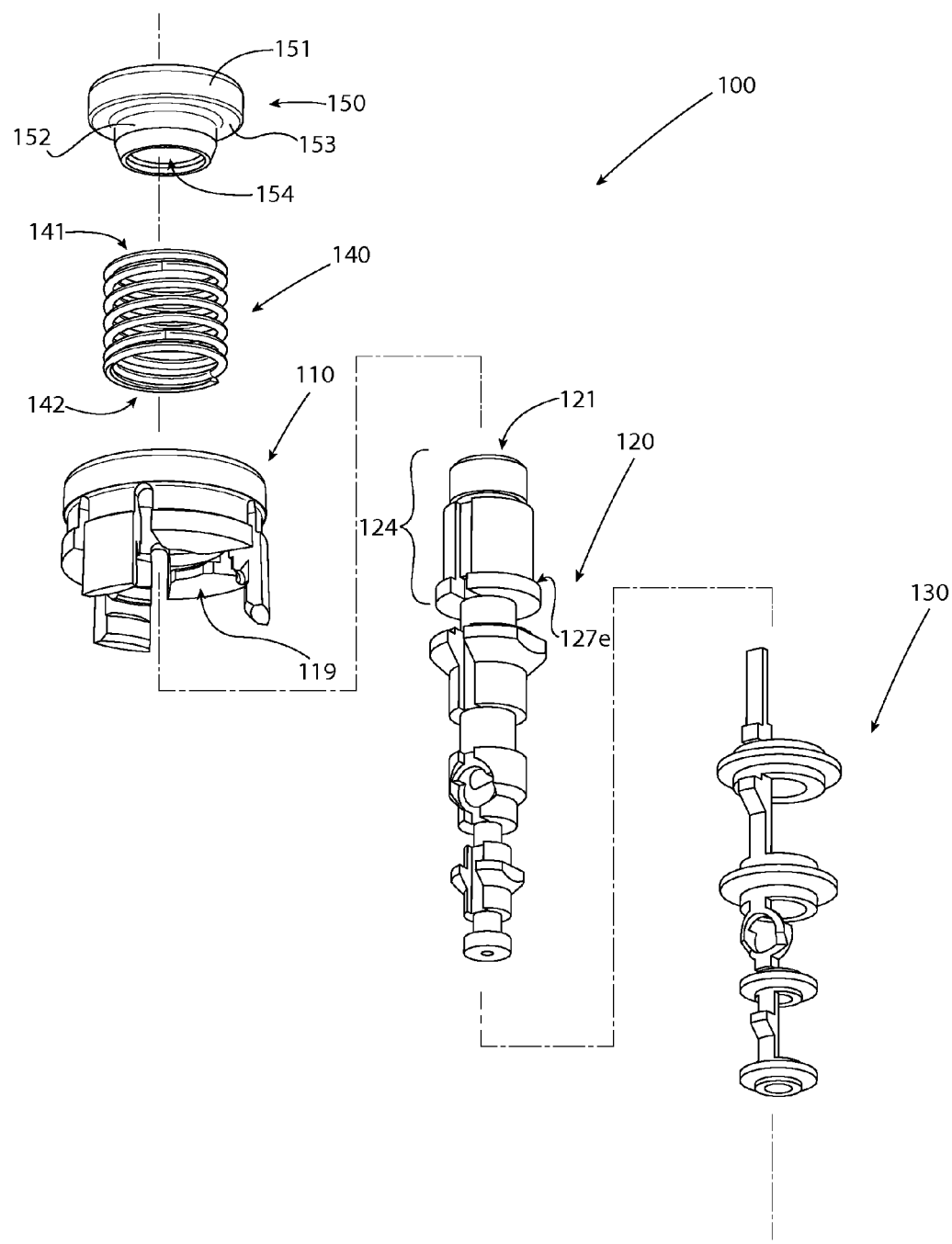
FIG. 6 shows an exploded view of the air/water valve assembly of FIG. 5 according to an exemplary embodiment of the present invention.
Figure 7A:
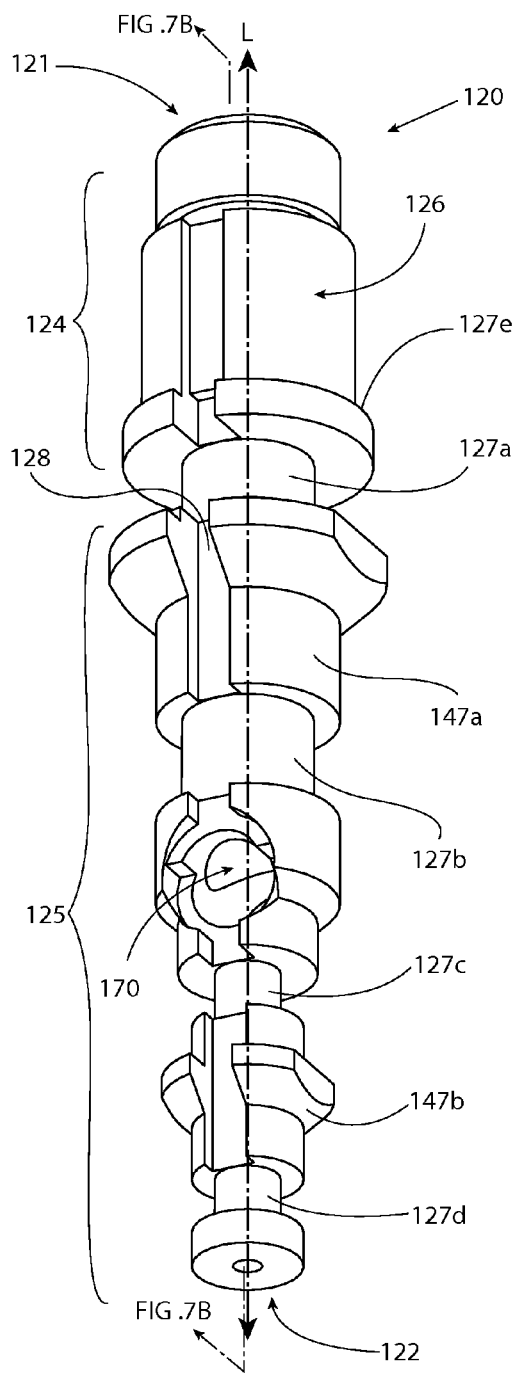
FIG. 7A shows a perspective view of a spool according to an exemplary embodiment of the present invention.
Figure 7B:
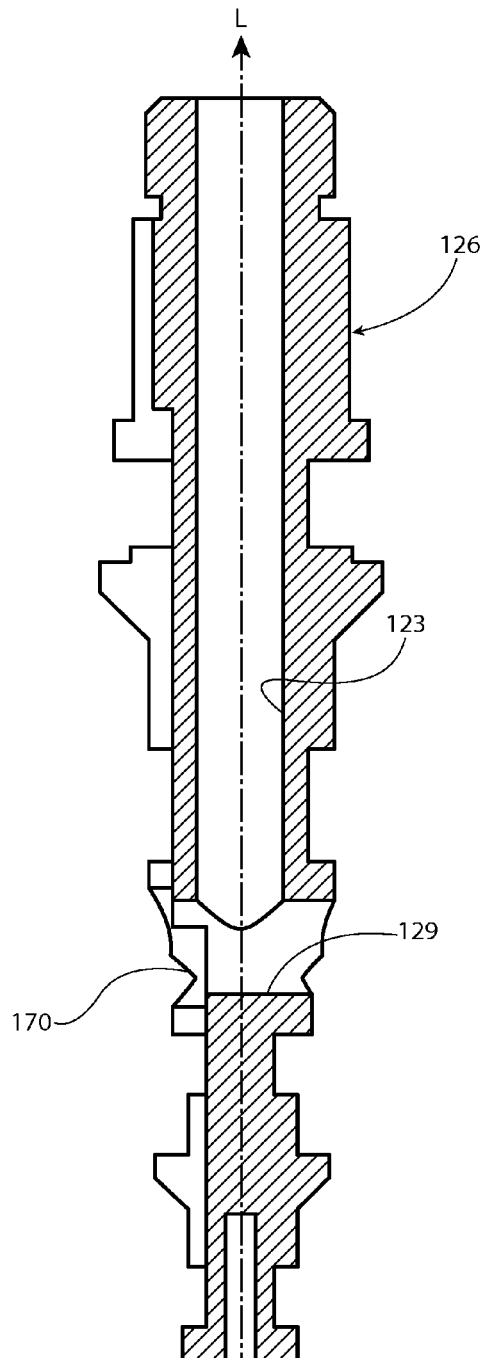
FIG. 7B shows a cross-sectional view of the spool of FIG. 7A.

Turning now to FIGS. 5 and 6, a valve assembly 100 is shown in accordance with embodiments of the present invention. In the depicted embodiment, the valve assembly 100 includes a housing 110, a spool 120, and a sealing member 130. With reference to FIGS. 7A and 7B, the spool 120 includes a first end 121, a second end 122, and a longitudinal passageway 123 extending between the first end and the second end. The spool 120 further comprises a first portion 124 proximate the first end 121 and a second portion 125 proximate the second end 122. The first portion 124 of the spool 120 may be configured to be received at least partially within the housing 110.

Moreover, an outer surface 126 of the spool 120 may define a plurality of bearing features 147a, 147b and/or a plurality of positioning features 127a, 127b, 127c, 127d. As depicted, the bearing features 147a, 147b and the positioning features 127a, 127b, 127c, 127d may provide the spool 120 with a surface profile such that the diameter of the spool varies along the spool's longitudinal axis L.

The bearing features 147a, 147b may, for example, comprise portions of the spool that bulge or otherwise protrude radially outwardly from the surface 126 of the spool 120, such that they provide regions of the spool that have a larger diameter than other regions of the spool (e.g., a larger diameter than adjacent regions). In this regard, the bearing features 147a, 147b may be configured (e.g., sized, shaped, and/or positioned) to serve a function similar to the bearings 66, 68 of the conventional valve shown in FIG. 4.

The positioning features 127a, 127b, 127c, 127d may, for example, comprise ridges, concavities, and/or other features that are configured to receive complementary portions of the sealing member 130, as described in greater detail below. For example, the positioning features 127a, 127b, 127c, 127d may be configured such that the material for forming the sealing rings 132, 133, 134, 135 of the sealing member may be injection molded into the positioning features.

Figure 8:
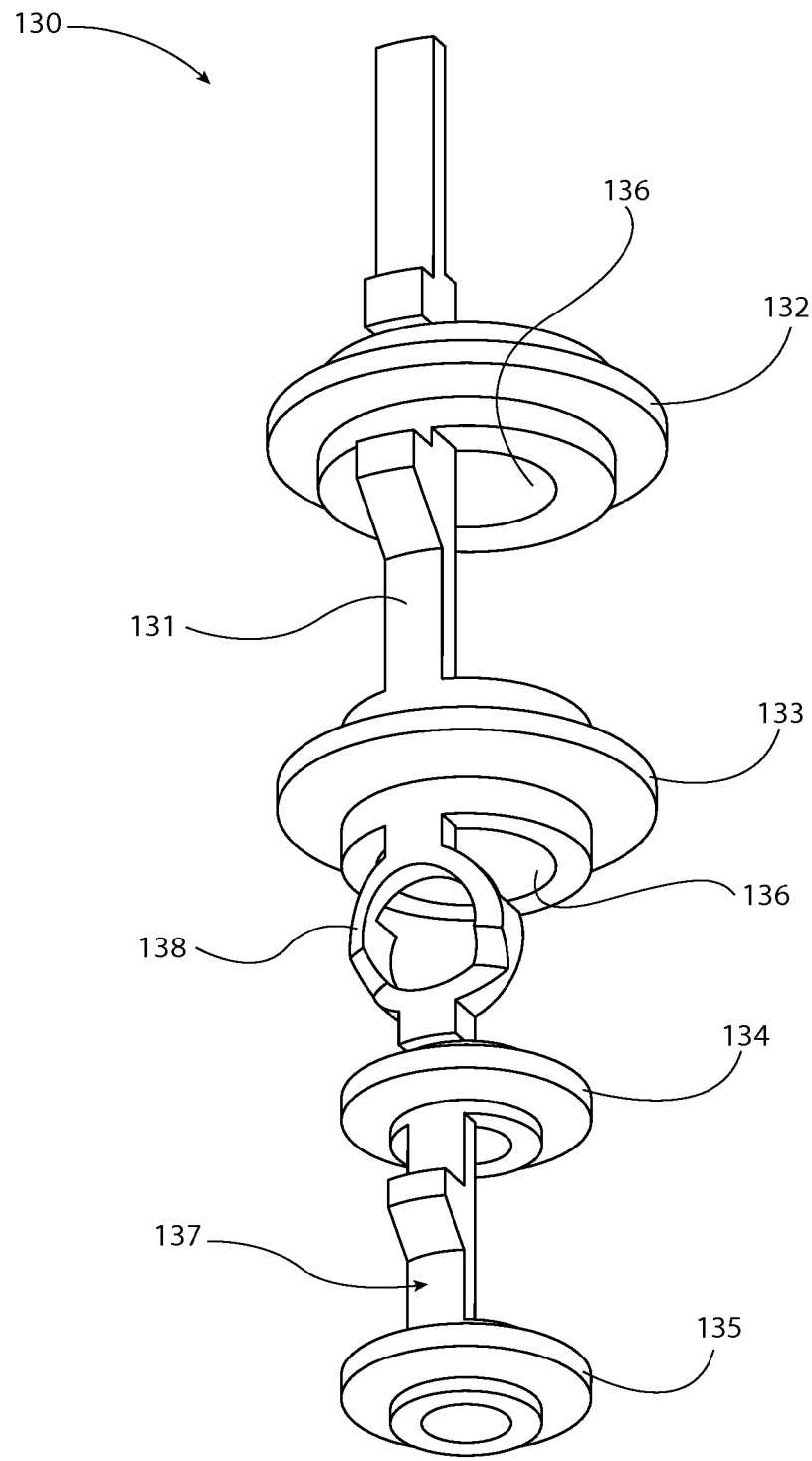
FIG. 8 shows a perspective view of a one-piece sealing member according to an exemplary embodiment of the present invention.

A close-up view of the sealing member 130 is shown in FIG. 8. The sealing member 130 may include a longitudinal support member 131 and a plurality of sealing rings extending circumferentially from the support member 131. In the depicted embodiment, the sealing member 130 includes four sealing rings 132, 133, 134, 135. Each sealing ring 132, 133, 134, 135 may, for example, be spaced from an adjacent sealing ring by a distance along a length of the support member 131 that corresponds to a distance between adjacent positioning features 127a, 127b, 127c, 127d. For example, referring to FIGS. 7A and 8, the positioning features 127a and 127b in FIG. 7A may correspond to the distance between sealing ring 132 and 133 in FIG. 8. Likewise, the distance between the positioning features 127b and 127c may correspond to the distance between the sealing rings 133 and 134, and the distance between the positioning features 127c and 127d may correspond to the distance between the sealing rings 134 and 135.

Accordingly, an inner surface 136 of the support member 131 may be configured to engage the outer surface 126 of the spool 120. For example, each sealing ring 132, 133, 134, and 135 may define an opening therethrough, such that an inner circumferential surface 136 of each sealing ring may be configured to sealingly engage the outer surface 126 of the second portion 125 of the spool 120 proximate a corresponding positioning feature 127a, 127b, 127c, 127d. In this way, the sealing rings 132, 133, 134, and 135 may be configured to serve as the seals 70, 72, 74, 76 of the conventional valve shown in FIG. 4 when assembled as a valve assembly and disposed within an air/water cylinder (such as the air/water cylinder 96 shown in FIGS. 2A and 2B). In contrast with the seals in a conventional valve, such as the valve 50 of FIGS. 2A and 2B, embodiments of the invention provide sealing rings 132, 133, 134, 135 that consist of only 1 piece of injection molded plastic that is, in some embodiments, overmolded directly onto the spool 120 in the configuration shown in FIG. 5, as described in greater detail below.

Turning again to FIG. 6, in some embodiments, the valve assembly 100 may further include a spring 140 and a retainer 150. Although a coil spring is depicted in FIG. 6, other types of spring structures and materials may be used in other embodiments to provide the same biasing forces. Thus, the spring 140 may be a coil spring (metal or plastic), a spring washer-type spring (metal or plastic), or a cylinder of foam material.

The spring 140 may have a first end 141 and a second end 142 and may be disposed around the first portion 124 of the spool 120, as shown in FIGS. 5 and 6. The retainer 150, in turn, may be configured (e.g., sized and shaped) to be received within the first end 141 of the spring 140 and to engage the first end 121 of the spool 120. For example, the retainer 150 may include a cap portion 151 and a reduced-diameter portion 152 extending from the cap portion. A lip 153 may be defined by the cap portion 151 proximate the interface between the cap portion and the reduced-diameter portion 152. The reduced-diameter portion 152 may be configured to fit inside the spring 140 (e.g., inside the coils of the spring in the depicted embodiment), and the first end 141 of the spring 140 may thus be configured to engage (e.g., contact and/or push against) the lip 153 when the valve assembly is assembled. Moreover, the reduced-diameter portion 152 may define an opening 154 therethrough that is configured to receive and engage at least part of the first portion 124 of the spool 120. For example, the spool 120 may be attached to the retainer 150 via a press fit engagement between the first end 121 of the spool and the opening 154 within which it is received. Additionally or alternatively, adhesive may be used to secure the first end 121 of the spool 120 within the opening 154 of the retainer 150. In such a way, the retainer 150 may be fixed with respect to the spool 120, and the spring 140 may be retained in a surrounding relationship with respect to the first portion 124 of the spool 120.

Figure 9:
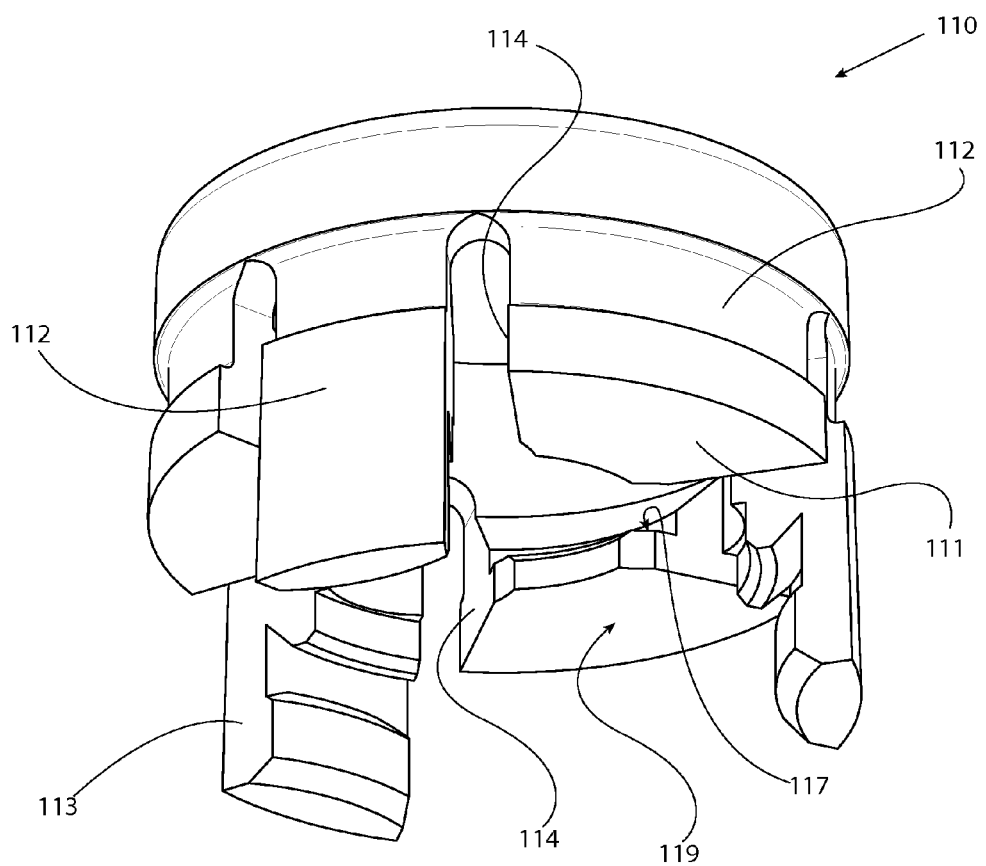
FIG. 9 shows a perspective view of a housing according to an exemplary embodiment of the present invention.

At the same time, the second end 142 of the spring 140 may be configured to engage and remain fixed with respect to the housing 110. For example, as shown in FIG. 9, in some embodiments, the housing 110 may define radial extensions 111 that extend inwardly from an outer wall 112 of the housing. The second end 142 of the spring 140 may, in such embodiments, engage and push against an inner surface 117 of the radial extensions 111 of the housing 110, shown in FIG. 9, such that an actuating force applied to the spring 140 (such as by pushing on the retainer 150 in the direction of the spool 120 in the assembled configuration shown in FIG. 5) is resisted by the radial extensions 111 and the spring 140 remains between the lip 153 of the retainer and the inner surface 117 of the radial extensions 111 of the housing. In the unactuated position shown in FIG. 5, the retainer 150 may be biased away from the housing 110. The retainer 150 and spool 120 assembly is maintained in engagement with the housing 110, however, through the engagement of a spool ledge 127e with an outer surface 119 of the radial extensions 11 of the housing 110 (shown in FIGS. 6, 7A, and 9).

Thus, with the second end 142 of the spring 140 engaged with the housing 110, the first end 141 of the spring engaged with the retainer 150, and the retainer engaged with the first end 121 of the spool, as described above, an actuating force applied to the retainer 150 when the valve assembly 100 is in the unactuated position shown in FIG. 5 serves to move the spool 120 and the sealing member 130 attached thereto in the direction indicated in FIG. 5 by the arrow 160. When the actuating force is removed, the biasing force of the spring 140 moves the spool 120 and sealing member 130 back towards the unactuated position depicted in FIG. 5. Accordingly, movement of the spool 120 and the sealing member 130 within an air/water cylinder such as the cylinder 96 shown in FIGS. 2A and 2B within an endoscope or other medical instrument may open and close certain air and water pathways, similarly to the function of the valve 50 described above with respect to FIGS. 2A and 2B.

Turning again now to FIG. 7A, in some embodiments, at least a portion of the outer surface 126 of the spool 120 may define a longitudinal groove 128 that is configured to receive the support member 131 of the sealing member 130 (shown in FIG. 8), as shown in the assembled configuration depicted in FIG. 5. The longitudinal groove 128 and the support member 131 may be configured, for example, such that the outer surface 137 of the support member 131 forms a flush surface with the outer surface 126 of the spool 120 when the sealing member 130 is engaged with the spool. As noted above, the tight fit of the sealing member 130 with the spool 120 (e.g., within the longitudinal groove 128) may, for example, be the result of the overmolding of the sealing member onto the spool, as described in greater detail below. In other cases, however, the sealing member 130 may be formed (e.g., molded) separately from the spool 120 and may be configured (e.g., through sizing and material selection) such that it can be stretched to fit onto the spool 120.

As shown in the cross-section of FIG. 7B, in some cases the spool 120 may define a transverse passageway 129 that is substantially perpendicular to and intersects with the longitudinal passageway 123. The transverse passageway 129 may be defined through the longitudinal passageway 123, so as to provide a flow path for the air or other gas to enter into the longitudinal passageway and be directed towards the first end 121 of the spool 120. The air or other gas may then be released to the external environment via opening 154 in the cap portion 152. In this regard, the transverse passageway may be defined through the longitudinal groove 128.

In still other embodiments, at least one portion of the longitudinal groove 128 may be defined by at least one positioning feature, as described above. For example, in the depicted embodiment of FIG. 7A, the longitudinal groove 128 extends through and is defined by the bearing features 147a, 147b and/or the positioning features 127a, 127b, 127c, 127d. Moreover, in some cases, such as when the transverse passageway 129 is defined through the longitudinal groove 128, the support member 131 of the sealing member 130 may define a longitudinally extending ring 138 that is configured to engage the opening 170 of the transverse passageway 129 defined in the outer surface 126 of the spool 120, as shown in FIG. 5. In other cases, however, such as when the transverse passageway 129 is not defined through the longitudinal groove 128 (e.g., when the location of the longitudinal groove is rotated 90° about the longitudinal axis L from the position depicted in FIG. 7A), the support member 131 of the sealing member 130 need not define a longitudinally extending ring 138 and may, instead, extend linearly from one end of the sealing member to the other.

Figure 10:
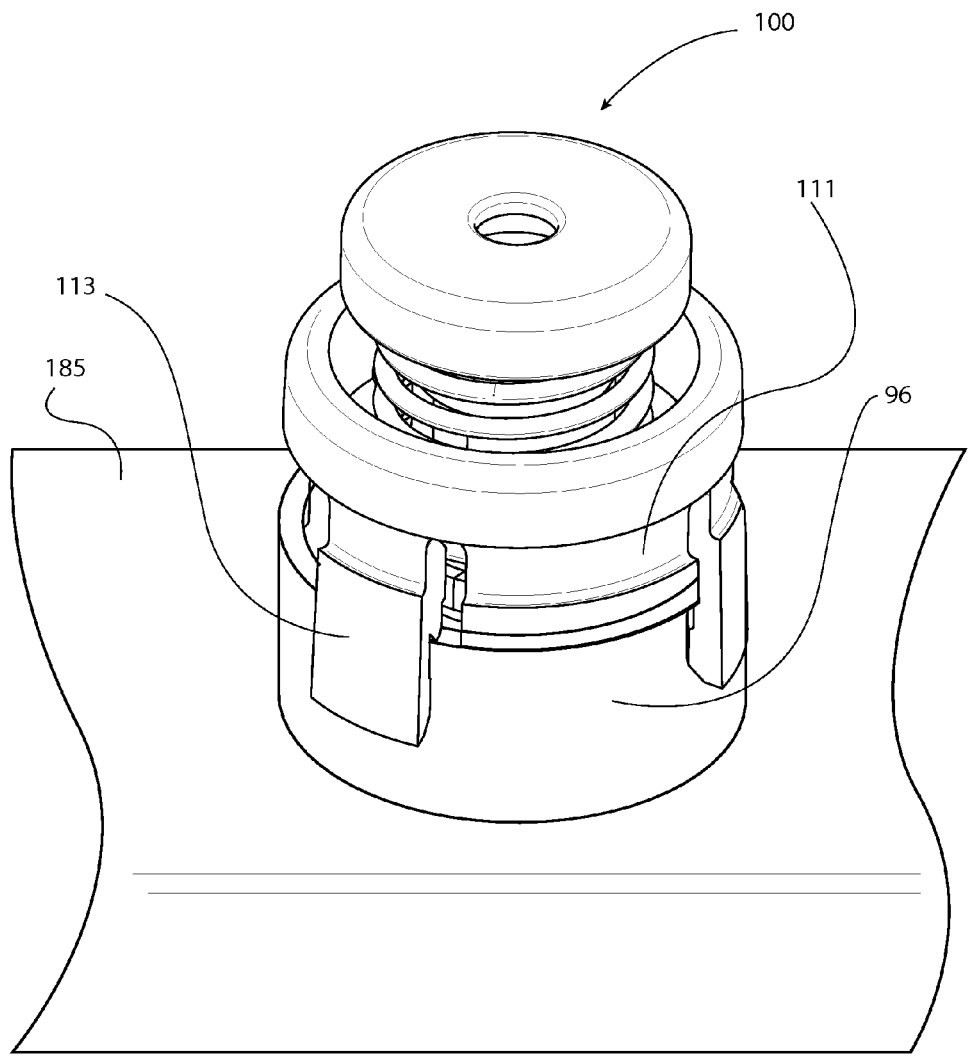
FIG. 10 shows a view of a valve assembly inserted within an air/water cylinder of a medical device according to an exemplary embodiment of the present invention.

With reference to FIG. 9, in some embodiments, the housing 110 defines at least one longitudinal extension 113 configured to extend over the outer surface 126 of the first portion of the spool 120 or at least a portion thereof, as shown in FIG. 5. In the depicted embodiment, for example, three longitudinal extensions 113 are provided, arranged in alternating fashion with portions of the outer wall 112 of the housing 110 that define three radial extensions 111. The longitudinal extensions 113 may be configured (e.g., sized and shaped) to secure the valve assembly 100 to an air/water cylinder of the endoscope or other medical device when the valve assembly is installed for use. With reference to FIG. 10, for example, the air/water cylinder 96 may extend upwardly from the body 185 of the endoscope or medical device, and the valve assembly 100 shown in FIG. 5 may be inserted into the air/water cylinder. As the valve assembly 100 is inserted into the air/water cylinder 96, the longitudinal extensions 113 may receive the air/water cylinder 96, and a top edge of the air/water cylinder may rest against the outer surface 119 of the radial extensions 111 of the housing 110 shown in FIG. 9 once the valve assembly 100 is fully engaged within the air/water cylinder. Accordingly, once the valve assembly 100 is inserted into the air/water cylinder 96, as depicted in FIG. 10, the longitudinal extensions 113 may form a snug fit with the outer surface of the air/water cylinder 96, thereby maintaining the valve assembly in engagement with the endoscope or other medical instrument during operation.

In some embodiments, slots 114 may be defined in the outer wall 112 of the housing 110. The slots 114 may be configured to facilitate engagement of the housing 110 with the air/water cylinder 96 by allowing the housing 110 of the valve assembly to form a positive lock with the endoscope or other medical instrument within which the valve assembly 100 is mounted. The slots 114, for example, may allow the longitudinal extensions 113 to act as tangs that are configured to be moved outwardly from the longitudinal axis of the valve assembly (e.g., by flexing) as the inner surface of the longitudinal extensions are guided over mating ridges defined by the outer surface of the air/water cylinder 96 as the valve assembly is inserted into an operating position therein. In other cases, however, the radial extensions 111 and the longitudinal extensions 113 may form a continuous outer wall 112 of the housing.

In some embodiments, one or more of the longitudinal extensions 113 may include a pull tab (not shown) on the outer surface of the respective longitudinal extension that can be grasped by a user and used to break off at least one of the longitudinal extensions once use of the valve assembly is compete. In this way, the valve assembly may be more easily removed from the endoscope after a single use (e.g., by "unlocking" the attachment of the valve assembly to the air/water cylinder). At the same time, the breaking of a longitudinal extension may prevent the use of the valve assembly in another endoscope for additional procedures, thereby ensuring that the valve assembly is a single-use valve assembly.

Figure 11:
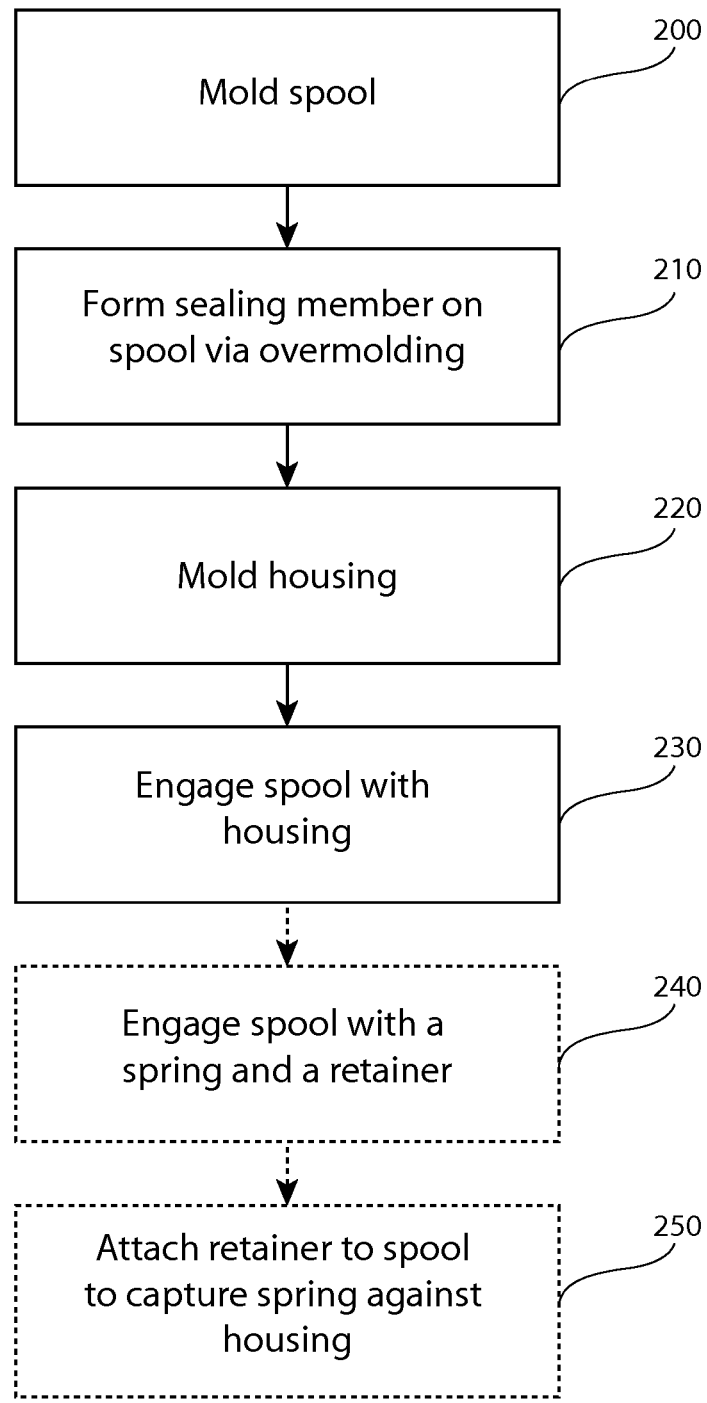
FIG. 11 illustrates a flowchart of a method for manufacturing an air/water valve assembly according to an exemplary embodiment of the present invention.

Turning now to FIG. 11, a method of making a valve assembly, such as the valve assembly 100 described above and illustrated in FIGS. 5-9, is shown. According to embodiments of the method, a spool is molded at block 200. As described above, the spool may include a first end, a second end, a longitudinal passageway extending between the first end and the second end, and first and second portions proximate the first and second ends, respectively, where an outer surface of the second portion of the spool defines a plurality of positioning features. The spool may be molded in a conventional mold. Suitable materials for molding the spool may include, for example, polycarbonate (PC); acrylonitrile butadiene styrene (ABS); polypropylene; polyethylene; and other suitable polymers.

Figure 12A:
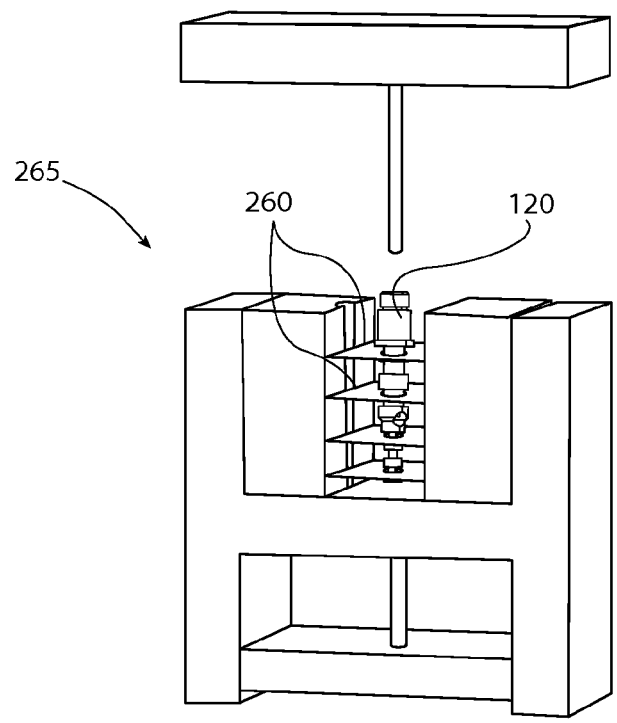
FIGS. 12A and 12B show schematic representations of a mold for manufacturing an air/water valve assembly according to an exemplary embodiment of the present invention.
Figure 12B:
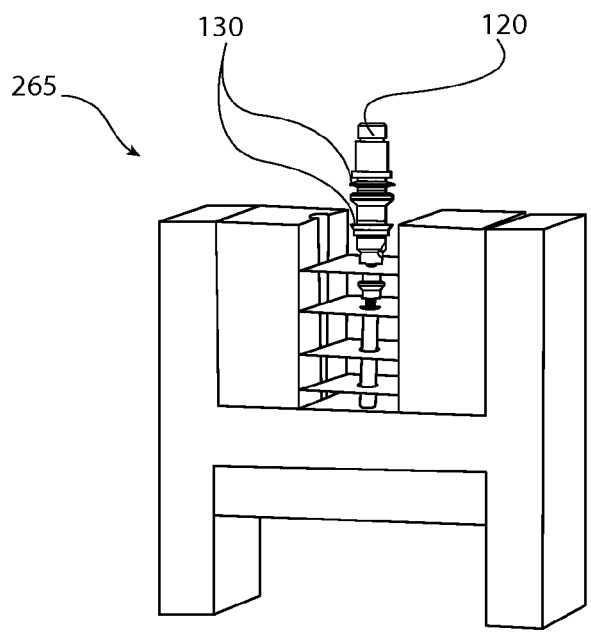

The spool may be removed from the first mold and placed in a second mold for overmolding the sealing member, as described at block 210. An illustration of an embodiment of the second mold 265 is shown in FIGS. 12A and 12B. The sealing member may be made of elastomeric materials and may include a longitudinal support member and a plurality of sealing rings extending circumferentially from the support member, as described above. Each sealing ring may be spaced from an adjacent sealing ring a distance along a length of the support member that corresponds to a distance between adjacent positioning features defined by the spool, such that an inner surface of the support member engages the outer surface of the spool. Each sealing ring may thus define an opening such that an inner circumferential surface of each sealing ring sealingly engages the outer surface of the second portion of the spool proximate a corresponding adjacent positioning feature. In some embodiments, stationary plates defining concentric holes may be arranged in a spaced apart manner along the longitudinal axis of the spool. The stationary plates 260 may be arranged in an orientation that is perpendicular to the longitudinal axis of the spool, and a portion of the spool 120 may be received within the hole defined in each plate at a location at which a sealing ring is to be formed, as shown in FIG. 12A. In this way, the stationary plates may allow seal contact surfaces (e.g., an outer circumferential surface) of the sealing rings to be formed during the overmolding process without the formation of parting lines, which may otherwise cause leaks. The completed spool 120 with overmolded sealing member 130 may then be removed from the mold 265 shown in FIG. 12A by ejecting the spool and sealing member through the stationary plates 260, as shown in FIG. 12B.

In some embodiments, molding the spool may include defining a transverse passageway that is substantially perpendicular to and intersects with the longitudinal passageway of the spool, as described above. The transverse passageway may be defined through the longitudinal groove in some cases. Moreover, in some instances, overmolding the sealing member may comprise defining a longitudinally extending ring in the support member that engages an opening of the transverse passageway defined in the outer surface of the spool.

At block 220, a housing may be molded, where the housing is configured to at least partially receive the first portion of the spool. The housing may be made of any suitable material, such as a thermoplastic or polyester-based elastomer (e.g., rubber, Viton® material, silicone, neoprene, polyolefin, etc.) or polyurethane. The spool may then be engaged with the housing at block 230. The first portion of the spool, for example, may be at least partially disposed within the housing, as described above.

In some embodiments, the spool may be engaged with a spring and a retainer at block 240, and the retainer may be attached to the spool to capture a spring between the housing and the retainer at block 250. For example, a spring may be disposed around the first portion of the spool. A retainer configured to be received by a first end of the spool may be provided, and the second end of the spring may be engaged to the housing such that a position of the second end of the spring remains fixed with respect to the housing. Likewise, the first end of the spring may be engaged with the retainer, and the retainer may be attached to the first end of the spool such that the retainer is biased away from the housing, as described in greater detail above.

It will be understood that each block or step of the flowchart illustration of FIG. 11, and combinations of blocks, can be implemented by computer program instructions. These computer program instructions may be loaded onto a computer or other programmable apparatus to produce a machine, such that the instructions which execute on the computer or other programmable apparatus form means for implementing the functions specified in the flowchart block(s) or step(s). These computer program instructions may also be stored in a computer-readable memory that can direct a computer or other programmable apparatus to function in a particular manner, such that the instructions stored in the computer-readable memory may produce an article of manufacture including instruction means which can implement the function specified in the flowchart block(s) or step(s). The computer program instructions may also be loaded onto a computer or other programmable apparatus, among other things, to cause a series of operational steps to be performed on the computer or other programmable apparatus. This may produce a computer implemented process such that the instructions which execute on the computer or other programmable apparatus provide steps for implementing the functions specified in the flowchart block(s) or step(s).

Accordingly, blocks or steps of the flowchart illustration support, among other things, combinations of means for performing the specified functions, combinations of steps for performing the specified functions and program instruction means for performing the specified functions. It will also be understood that each block or step of the flowchart illustration, and combinations thereof, can be implemented by special purpose hardware-based computer systems which perform the specified functions or steps, or combinations of special purpose hardware and computer instructions.

As described above and shown in the associated figures, embodiments of the air/water valve assembly are configured to be disposable, such that the valve assemblies may be removed from an endoscope or other medical equipment and disposed of after use in a single procedure. Accordingly, embodiments of the valve assembly described above do not include numerous precision-machined metal components or multiple separate seals that need to be assembled, nor does the valve assembly require adhesive for attaching machined parts together, which can be complicated and costly. Rather, embodiments of the invention reduce the parts count of the assembly to 5 parts, while still allowing for compatibility of the valve assembly with existing valve bodies. Moreover, embodiments of the valve assembly make use of high volume production processes such as injection molding to minimize manufacturing costs. In addition, the shorter duty life allows for less expensive materials to be used, as the valve assembly does not need to withstand repeated use.

Other modifications and other embodiments of the invention set forth herein will come to mind to one skilled in the art to which this invention pertains having the benefit of the teachings presented in the foregoing descriptions and on the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Further, throughout the description, where compositions are described as having, including, or comprising specific components, or where processes systems or methods are described as having, including, or comprising specific steps, it is contemplated that compositions or the present invention may also consist essentially of, or consist of the recited components, and that the processes or methods of the present invention also consist essentially or consist of the recited steps. Further, it should be understood that the order of steps or order of performing certain actions are immaterial so long as the invention remains operable. Moreover, two or more steps or actions may be conducted simultaneously with respect to the invention disclosed herein.

What is claimed is:

1. A valve assembly for a medical instrument comprising:
a housing;
a spool comprising a first end, a second end, a longitudinal passageway extending between the first end and the second end, and first and second portions proximate the first and second ends, respectively, wherein the first portion of the spool is configured to be received at least partially within the housing, and wherein an outer surface of the second portion of the spool defines a plurality of positioning features; and
a sealing member comprising a longitudinal support member and a plurality of sealing rings extending circumferentially from the support member, wherein each sealing ring is spaced from an adjacent sealing ring a distance along a length of the support member that corresponds to a distance between adjacent positioning features,
wherein an inner surface of the support member is configured to engage the outer surface of the spool, and
wherein each sealing ring defines an opening such that an inner circumferential surface of each sealing ring is configured to sealingly engage the outer surface of the second portion of the spool proximate a corresponding positioning feature.

2. The valve assembly of claim 1 further comprising:
a spring comprising a first end and a second end, wherein the spring is disposed around the first portion of the spool, and
a retainer configured to be received by the first end of the spool,
wherein the second end of the spring is configured to engage and remain fixed with respect to the housing, and the first end of the spring is configured to engage the retainer, such that the retainer is biased away from the housing.

3. The valve assembly of claim 2, wherein the housing defines at least one radial extension configured to engage the second end of the spring.

4. The valve assembly of claim 1, wherein at least a portion of the outer surface of the spool defines a longitudinal groove configured to receive the support member of the sealing member.

5. The valve assembly of claim 4, wherein an outer surface of the support member forms a flush surface with the outer surface of the spool when the sealing member is engaged with the spool.

6. The valve assembly of claim 4, wherein the sealing member is overmolded onto the spool.

7. The valve assembly of claim 4, wherein the spool defines a transverse passageway that is substantially perpendicular and intersects with the longitudinal passageway, and wherein the transverse passageway is defined through the longitudinal groove.

8. The valve assembly of claim 4, wherein at least one portion of the longitudinal groove is defined by at least one positioning feature.

9. The valve assembly of claim 1, wherein the spool defines a transverse passageway that is substantially perpendicular to and intersects with the longitudinal passageway, and wherein the support member of the sealing member defines a longitudinally extending ring configured to engage an opening of the transverse passageway defined in the outer surface of the spool.

10. The valve assembly of claim 1, wherein the sealing member comprises four sealing rings.

11. The valve assembly of claim 1, wherein the housing defines longitudinal extensions configured to engage the medical instrument within which the valve assembly is mounted.

12. A method of manufacturing a valve assembly for a medical instrument comprising:

molding a spool, wherein the spool comprises a first end, a second end, a longitudinal passageway extending between the first end and the second end, and first and second portions proximate the first and second ends, respectively, wherein an outer surface of the second portion of the spool defines a plurality of positioning features;

overmolding a sealing member onto an outer surface of the spool, wherein the sealing member comprises a longitudinal support member and a plurality of sealing rings extending circumferentially from the support member, wherein each sealing ring is spaced from an adjacent sealing ring a distance along a length of the support member that corresponds to a distance between adjacent positioning features, wherein an inner surface of the support member engages the outer surface of the spool, and wherein each sealing ring defines an opening such that an inner circumferential surface of each sealing ring sealingly engages the outer surface of the second portion of the spool proximate a corresponding positioning feature;

molding a housing configured to at least partially receive the first portion of the spool; and disposing the first portion of the spool at least partially within the housing.

13. The method of claim 12 further comprising:

disposing a spring around the first portion of the spool, wherein the spring defines a first end and a second end;

providing a retainer configured to be received by the first end of the spool;

engaging the second end of the spring to the housing such that a position of the second end of the spring remains fixed with respect to the housing;

engaging the first end of the spring with the retainer; and attaching the retainer to the first end of the spool, such that the retainer is biased away from the housing.

14. The method of claim 12 further comprising defining a longitudinal groove in at least a portion of the outer surface of the spool, wherein the longitudinal groove is configured to receive the support member of the sealing member.

15. The method of claim 14, wherein molding the spool comprises using a first mold to form the spool, and wherein overmolding the sealing member comprises removing the spool from the first mold and placing the spool in a second mold.

16. The method of claim 15, wherein overmolding the sealing member comprises directing an elastomeric material into the longitudinal groove to form the sealing member in the second mold.

17. The method of claim 15 further comprising arranging a plurality of stationary plates in an orientation that is perpendicular to a longitudinal axis of the spool, wherein the plates comprise concentric holes and are positioned at locations corresponding to locations of the sealing rings to be formed.

18. The method of claim 14, wherein molding the spool comprises defining a transverse passageway that is substantially perpendicular to and intersects with the longitudinal passageway, and wherein the transverse passageway is defined through the longitudinal groove.

19. The method of claim 14, wherein at least one portion of the longitudinal groove is defined by at least one positioning feature.

20. The method of claim 12, wherein molding the spool comprises defining a transverse passageway that is substantially perpendicular and intersects with the longitudinal passageway, and wherein overmolding the sealing member comprises defining a longitudinally extending ring in the support member that engages an opening of the transverse passageway defined in the outer surface of the spool.

* * * * *